United States Patent
Handa et al.

(10) Patent No.: US 11,594,208 B2
(45) Date of Patent: Feb. 28, 2023

(54) INFORMATION PROCESSING DEVICE, SOUND MASKING SYSTEM, CONTROL METHOD, AND RECORDING MEDIUM

(71) Applicant: Mitsubishi Electric Corporation, Tokyo (JP)

(72) Inventors: Kaori Handa, Tokyo (JP); Masaru Kimura, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 17/518,064

(22) Filed: Nov. 3, 2021

(65) Prior Publication Data

US 2022/0059067 A1    Feb. 24, 2022

Related U.S. Application Data

(63) Continuation of application No. PCT/JP2019/020243, filed on May 22, 2019.

(51) Int. Cl.
| | |
|---|---|
| *G10K 11/175* | (2006.01) |
| *G10L 25/63* | (2013.01) |
| *G10L 25/66* | (2013.01) |

(52) U.S. Cl.
CPC .......... *G10K 11/1754* (2020.05); *G10L 25/63* (2013.01); *G10L 25/66* (2013.01)

(58) Field of Classification Search
CPC ............. G10K 11/1754; G10K 11/175; G10K 11/1752; G10L 25/63; G10L 25/66
See application file for complete search history.

(56) References Cited

U.S. PATENT DOCUMENTS 5,755,674 A  *  5/1998  Watson .................. A61B 5/375
                                                          600/595
2018/0078732 A1    3/2018  Keshavan et al.
(Continued)

FOREIGN PATENT DOCUMENTS

| JP | 2008-15191 A | 1/2008 |
|---|---|---|
| JP | 2013-7911 A | 1/2013 |

(Continued)

OTHER PUBLICATIONS

Australian Office Action for Australian Application No. 2019446488, dated Apr. 8, 2022.
(Continued)

*Primary Examiner* — David L Ton
(74) *Attorney, Agent, or Firm* — Birch, Stewart, Kolasch & Birch, LLP

(57) ABSTRACT

An information processing device includes a first acquisition unit that acquires biological information on a user, a first judgment execution unit that executes a first judgment on whether a first discomfort condition is satisfied or not based on first discomfort condition information specifying the first discomfort condition and the biological information, a second acquisition unit that acquires a sound signal, an acoustic feature detection unit that detects an acoustic feature based on the sound signal, a second judgment execution unit that executes a second judgment on whether a second discomfort condition is satisfied or not based on second discomfort condition information specifying the second discomfort condition and the acoustic feature, and an output judgment unit that judges whether first masking sound should be outputted or not based on a result of the first judgment and a result of the second judgment.

9 Claims, 5 Drawing Sheets

(56) References Cited

U.S. PATENT DOCUMENTS

| | | | |
|---|---|---|---|
| 2018/0122353 A1 | 5/2018 | Braasch et al. | |
| 2019/0073990 A1 | 3/2019 | Moss et al. | |
| 2020/0367810 A1* | 11/2020 | Shouldice | G16H 50/20 |
| 2022/0059068 A1* | 2/2022 | Handa | G10K 11/1752 |
| 2022/0126056 A1* | 4/2022 | Wilkerson | A61M 16/06 |

FOREIGN PATENT DOCUMENTS

| | | | |
|---|---|---|---|
| JP | 2014-154483 A | 8/2014 | |
| JP | 6140469 B2 | 5/2017 | |

OTHER PUBLICATIONS

Extended European Search Report for European Application No. 19930120.1, dated Mar. 16, 2022.

European Communication pursuant to Article 94(3) EPC for corresponding European Application No. 19930120.1, dated Sep. 26, 2022.

* cited by examiner

INFORMATION PROCESSING DEVICE, SOUND MASKING SYSTEM, CONTROL METHOD, AND RECORDING MEDIUM

CROSS-REFERENCE TO RELATED APPLICATION

This application is a continuation application of International Application No. PCT/JP2019/020243 having an international filing date of May 22, 2019, the disclosure of which is incorporated herein by reference in its entirety.

BACKGROUND OF THE INVENTION

1. Field of the Invention

The present disclosure relates to an information processing device, a sound masking system, a control method and a recording medium storing a control program.

2. Description of the Related Art

Sound occurs in places like offices. For example, the sound is voice, typing noise or the like. A user's ability to concentrate is deteriorated by sound. In such a circumstance, a sound masking system is used. The deterioration in the user's ability to concentrate can be prevented by using the sound masking system.

Here, a technology regarding the sound masking system has been proposed (see Patent Reference 1: Japanese Patent Application Publication No. 2014-154483).

Incidentally, there are cases where the sound masking system is controlled based on the volume level of sound acquired by a microphone. However, there is a problem in that this control does not take the user's condition into consideration.

SUMMARY OF THE INVENTION

An object of the present disclosure is to execute sound masking control based on the user's condition.

An information processing device according to an aspect of the present disclosure is provided. The information processing device includes a first acquisition unit that acquires biological information on a user acquired by a biological information acquisition device, a first judgment execution unit that executes a first judgment on whether a first discomfort condition as a discomfort condition corresponding to the biological information is satisfied or not based on first discomfort condition information specifying the first discomfort condition and the biological information acquired by the first acquisition unit, a second acquisition unit that acquires a sound signal outputted from a microphone, an acoustic feature detection unit that detects an acoustic feature based on the sound signal, a second judgment execution unit that executes a second judgment on whether a second discomfort condition as a discomfort condition corresponding to the acoustic feature is satisfied or not based on second discomfort condition information specifying the second discomfort condition and the acoustic feature detected by the acoustic feature detection unit, and an output judgment unit that judges whether first masking sound should be outputted or not based on a result of the first judgment and a result of the second judgment.

According to the present disclosure, it is possible to execute sound masking control based on the user's condition.

BRIEF DESCRIPTION OF THE DRAWINGS

The present disclosure will become more fully understood from the detailed description given hereinbelow and the accompanying drawings which are given by way of illustration only, and thus are not limitative of the present disclosure, and wherein.

DETAILED DESCRIPTION OF THE INVENTION

Embodiments will be described below with reference to the drawings. The following embodiments are just examples and a variety of modifications are possible within the scope of the present disclosure.

First Embodiment

Figure 1:
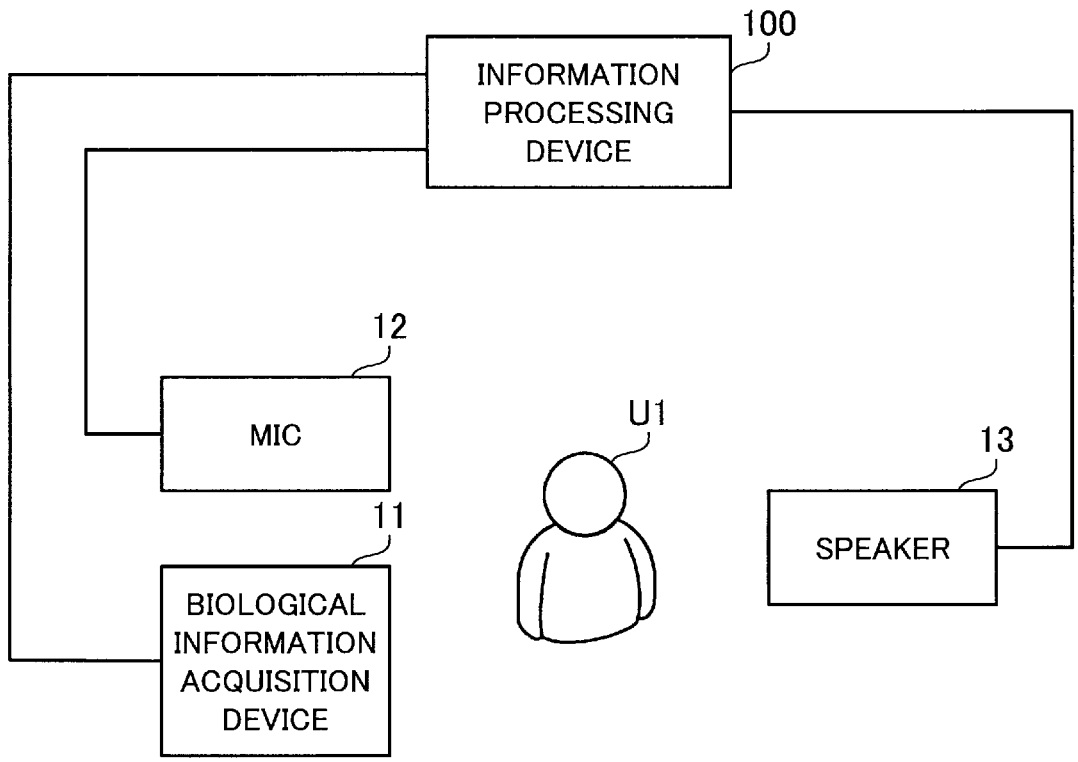
FIG. 1 is a diagram showing a sound masking system in a first embodiment.

FIG. 1 is a diagram showing a sound masking system in a first embodiment. The sound masking system includes an information processing device 100 and a speaker 13. Further, the sound masking system may include a biological information acquisition device 11 and a mic 12. Here, the mic is a microphone. The microphone will hereinafter be referred to as a mic.

For example, the mic 12 and the speaker 13 are installed in an office. The information processing device 100 is installed in the office or in a place other than the office. The information processing device 100 is a device that executes a control method.

FIG. 1 shows a user U1. In the following description, the user U1 is assumed to be in the office.

The biological information acquisition device 11 acquires biological information on the user U1. When the biological information is a brain wave (unit: μV), for example, the biological information acquisition device 11 is a simple electroencephalograph or a multi-channel electroencephalograph. When the biological information is a brain blood flow (unit: mM or mm), for example, the biological information acquisition device 11 is an optical topography apparatus. When the biological information is an electrocardiogram (unit: mV), for example, the biological information acquisition device 11 is an electrocardiograph. When the biological information is a heart rate (unit: times or bpm), for example, the biological information acquisition device 11 is a heart rate meter or a pulsimeter. When the biological information is cardiac sound (unit: times or bpm), for example, the biological information acquisition device 11 is a stethoscope or a mic. Incidentally, this mic can be different from the mic 12. When the biological information is a pulse wave (unit: amplitude value), the biological information acquisition device 11 is a sphygmograph. When the biological information is nictation (unit: times) or the length between the upper eyelid and the lower eyelid (unit: mm), the biological information acquisition device 11 is a sight line measurement system, a camera or an electrooculography. When the biological information is ocular potential (unit: μV), for example, the biological information acquisition device 11 is an electrooculography. When the biological information is a pupil diameter (unit: mm), for example, the biological information acquisition device 11 is a sight line measurement system. When the biological information is the user U1's line of sight, for example, the biological information acquisition device 11 is a sight line measurement system. Incidentally, the user U1's line of sight is represented by coordinates. When the biological information is myoelectric potential (unit: μV), for example, the biological information acquisition device 11 is an electromyograph. When the biological information is cutaneous electrical potential (unit: V), for example, the biological information acquisition device 11 is a cutaneous electrometer. When the biological information is skin conductance (unit: μS), for example, the biological information acquisition device 11 is a skin conductance measurement device. When the biological information is blood pressure (unit: mmHg), for example, the biological information acquisition device 11 is a blood pressure gauge. When the biological information is body temperature (unit: ° C.), for example, the biological information acquisition device 11 is a clinical thermometer or a dermatherm. When the biological information is perspiration (unit: mg), for example, the biological information acquisition device 11 is a diaphoremeter. When the biological information is the user U1's voice, for example, the biological information acquisition device 11 is a mic. Incidentally, this mic can be different from the mic 12. When the biological information is the user U1's motion such as the number of steps, for example, the biological information acquisition device 11 is a camera, a motion capture system or an acceleration sensor. When the biological information is the user U1's position, for example, the biological information acquisition device 11 is a beacon positioning device or a Wireless Fidelity (WiFi) positioning device. Incidentally, WiFi is a registered trademark. When the biological information is the user U1's facial expression, for example, the biological information acquisition device 11 is a camera. When the biological information is the user U1's smell, for example, the biological information acquisition device 11 is an odor measuring device. When the biological information is the user U1's expiration, for example, the biological information acquisition device 11 is an expiration sensor. When the biological information is the user U1's breathing rate, breathing cycle or breathing quantity, for example, the biological information acquisition device 11 is a stethoscope. When the biological information is salivary amylase (unit: KIU/L), for example, the biological information acquisition device 11 is a salivary amylase monitor.

The mic 12 acquires sound. Incidentally, this sound may be represented as environmental sound. The speaker 13 outputs masking sound.

Next, hardware included in the information processing device 100 will be described below.

Figure 2:
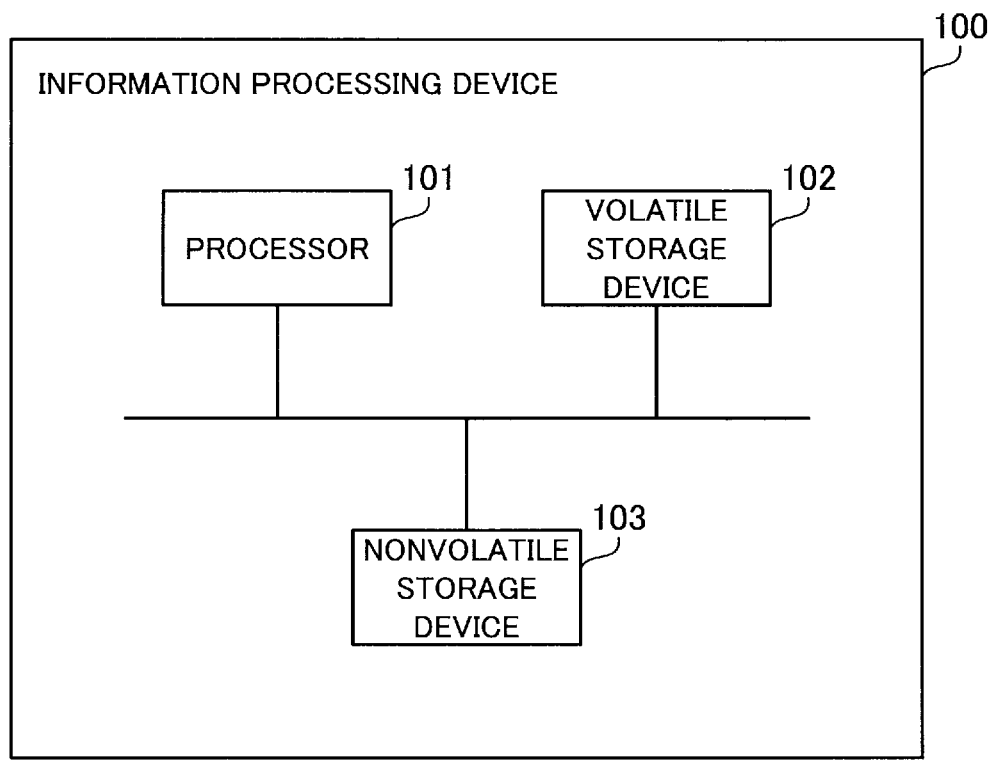
FIG. 2 is a diagram showing a configuration of hardware included in an information processing device in the first embodiment.

FIG. 2 is a diagram showing the configuration of the hardware included in the information processing device in the first embodiment. The information processing device 100 includes a processor 101, a volatile storage device 102 and a nonvolatile storage device 103.

The processor 101 controls the whole of the information processing device 100. For example, the processor 101 is a Central Processing Unit (CPU), a Field Programmable Gate Array (FPGA) or the like. The processor 101 can also be a multiprocessor. The information processing device 100 may be implemented by a processing circuitry or may be implemented by software, firmware or a combination of software and firmware. Incidentally, the processing circuitry can be either a single circuit or a combined circuit.

The volatile storage device 102 is main storage of the information processing device 100. For example, the volatile storage device 102 is a Random Access Memory (RAM). The nonvolatile storage device 103 is auxiliary storage of the information processing device 100. For example, the nonvolatile storage device 103 is a Hard Disk Drive (HDD) or a Solid State Drive (SSD).

Figure 3:
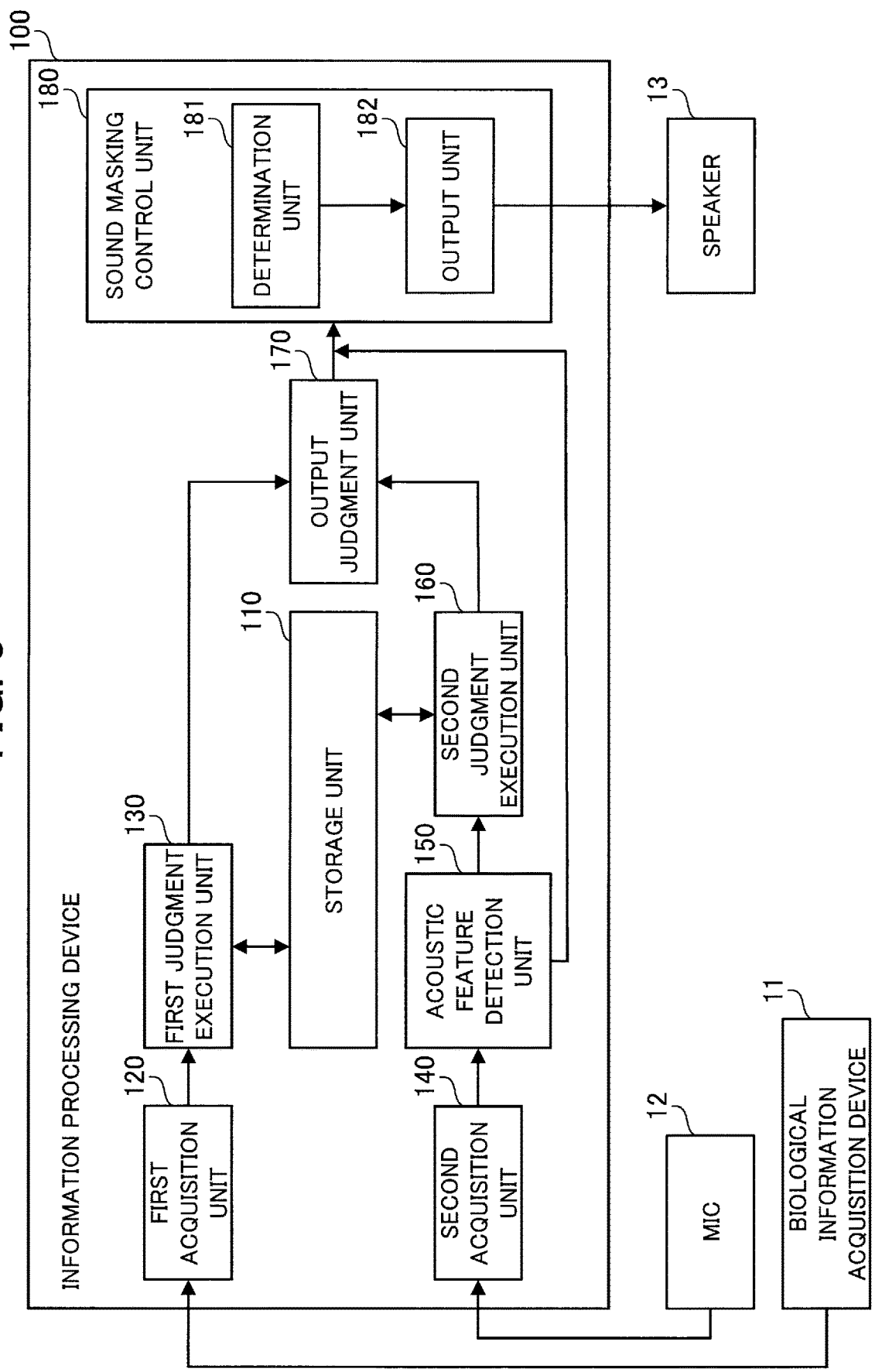
FIG. 3 is a functional block diagram showing a configuration of the information processing device in the first embodiment.

FIG. 3 is a functional block diagram showing the configuration of the information processing device in the first embodiment. The information processing device 100 includes a storage unit 110, a first acquisition unit 120, a first judgment execution unit 130, a second acquisition unit 140, an acoustic feature detection unit 150, a second judgment execution unit 160, an output judgment unit 170 and a sound masking control unit 180. The sound masking control unit 180 includes a determination unit 181 and an output unit 182.

The storage unit 110 may be implemented as a storage area secured in the volatile storage device 102 or the nonvolatile storage device 103.

Part or all of the first acquisition unit 120, the first judgment execution unit 130, the second acquisition unit 140, the acoustic feature detection unit 150, the second judgment execution unit 160, the output judgment unit 170 and the sound masking control unit 180 may be implemented by the processor 101.

Part or all of the first acquisition unit 120, the first judgment execution unit 130, the second acquisition unit 140, the acoustic feature detection unit 150, the second judgment execution unit 160, the output judgment unit 170 and the sound masking control unit 180 may be implemented as modules of a program executed by the processor 101. For example, the program executed by the processor 101 is referred to also as a control program. The control program has been recorded in a record medium, for example.

The storage unit 110 stores first discomfort condition information and second discomfort condition information. The first discomfort condition information specifies a first discomfort condition as a discomfort condition corresponding to the biological information. It can be expressed that the first discomfort condition information specifies a first discomfort condition as a discomfort condition using the biological information. For example, when the biological information is the active mass of a corrugator muscle, the first discomfort condition information indicates that discomfort exists when the active mass of the corrugator muscle is higher than or equal to a threshold value (i.e., when the glabella is wrinkled).

The second discomfort condition information will be explained in detail later.

The first acquisition unit 120 acquires the user U1's biological information acquired by the biological information acquisition device 11.

The first judgment execution unit 130 executes a first judgment on whether the first discomfort condition is satisfied or not based on the first discomfort condition information and the biological information acquired by the first acquisition unit 120. Incidentally, the first judgment may also be expressed as a judgment on whether the user U1 is uncomfortable or not.

When the biological information is the user U1's voice, for example, the first discomfort condition information is a feature value indicating discomfort obtained by an experiment or the like. The first judgment execution unit 130 executes an emotion recognition process based on the user U1's voice. Based on the first discomfort condition information and the result of executing the emotion recognition process, the first judgment execution unit 130 executes the judgment on whether the user U1 is uncomfortable or not.

When the biological information is the user U1's facial expression, for example, the first discomfort condition information indicates an angry face, a face with the glabella wrinkled, or the like. The first judgment execution unit 130 judges the user U1's facial expression by using image recognition technology. Based on the first discomfort condition information and the result of the judgment, the first judgment execution unit 130 executes the judgment on whether the user U1 is uncomfortable or not.

The second acquisition unit 140 acquires a sound signal outputted from the mic 12. The acoustic feature detection unit 150 detects acoustic features based on the sound signal. For example, the acoustic features are a frequency, a sound pressure level, fluctuation strength, a direction in which a sound source exists, and so forth.

Here, the second discomfort condition information will be explained. The second discomfort condition information specifies a second discomfort condition as a discomfort condition corresponding to an acoustic feature. The second discomfort condition information may also be expressed as specifying a second discomfort condition as a discomfort condition using an acoustic feature. The second discomfort condition is a condition in which a human generally feels uncomfortable. For example, when the acoustic feature is the sound pressure level, the second discomfort condition indicates that the sound pressure level is higher than or equal to a certain value. Specifically, the second discomfort condition indicates that the sound pressure level is higher than or equal to 85 dB.

Incidentally, the first discomfort condition and the second discomfort condition may be conditions using a threshold value or a range.

The second judgment execution unit 160 executes a second judgment on whether the second discomfort condition is satisfied or not based on the second discomfort condition information and the acoustic features detected by the acoustic feature detection unit 150.

The output judgment unit 170 judges whether the masking sound should be outputted or not based on the result of the first judgment and the result of the second judgment. When the result of the first judgment indicates that the first discomfort condition is satisfied and the result of the second judgment indicates that the second discomfort condition is satisfied, the output judgment unit 170 judges that the masking sound should be outputted.

There is also a case where masking sound is already being outputted from the speaker 13 when the output judgment unit 170 executes the judgment process. In such the case, it can be expressed that the output judgment unit 170 judges whether new masking sound should be outputted or not based on the result of the first judgment and the result of the second judgment.

When it is judged that the masking sound should be outputted, the sound masking control unit 180 has masking sound based on the acoustic features outputted from the speaker 13. Specifically, processes executed by the sound masking control unit 180 are executed by the determination unit 181 and the output unit 182. The processes executed by the determination unit 181 and the output unit 182 will be described later. Incidentally, the masking sound is referred to also as first masking sound.

Next, a process executed by the information processing device 100 will be described below by using a flowchart.

Figure 4:
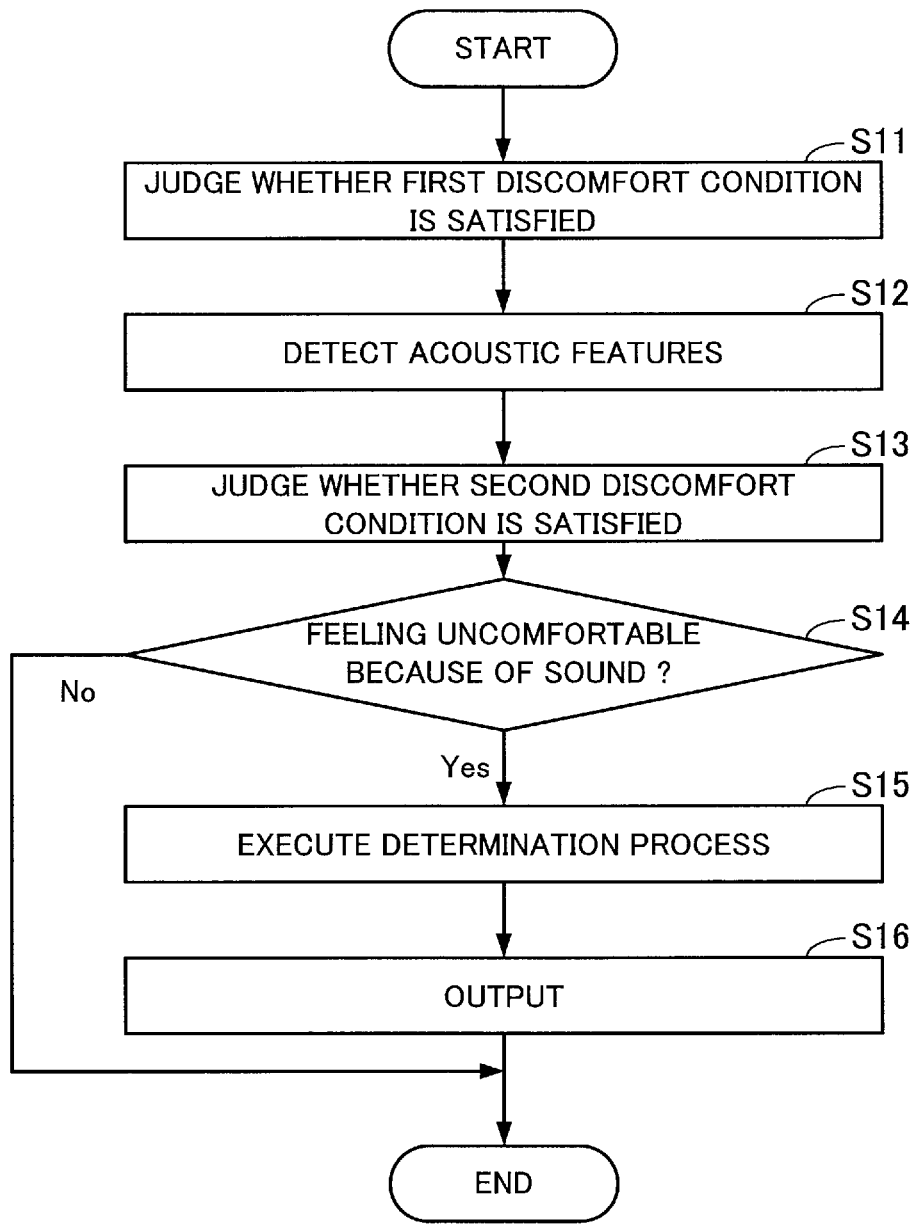
FIG. 4 is a flowchart showing a process executed by the information processing device in the first embodiment.

FIG. 4 is a flowchart showing the process executed by the information processing device in the first embodiment. The process of FIG. 4 is started when the first acquisition unit 120 has acquired the biological information and the second acquisition unit 140 has acquired the sound signal. Thus, there are cases where the process of FIG. 4 is started in a state in which the speaker 13 is outputting no masking sound. There are also cases where the process of FIG. 4 is started in a state in which the speaker 13 is outputting masking sound.

(Step S11) The first judgment execution unit 130 executes the first judgment on whether the first discomfort condition is satisfied or not based on the first discomfort condition information and the biological information acquired by the first acquisition unit 120. Namely, the first judgment execution unit 130 judges whether the user U1 is feeling uncomfortable or not based on the first discomfort condition information and the biological information acquired by the first acquisition unit 120.

(Step S12) The acoustic feature detection unit 150 detects acoustic features based on the sound signal acquired by the second acquisition unit 140.

(Step S13) The second judgment execution unit 160 executes the second judgment on whether the second discomfort condition is satisfied or not based on the second discomfort condition information and the acoustic features detected by the acoustic feature detection unit 150.

Here, it is also possible to execute the steps S12 and S13 before the step S11.

(Step S14) The output judgment unit 170 judges whether or not the user U1 is feeling discomfort because of sound. Specifically, when the result of the first judgment indicates that the first discomfort condition is satisfied and the result of the second judgment indicates that the second discomfort condition is satisfied, the output judgment unit 170 judges that the user U1 is feeling discomfort because of sound.

In the case where the result of the first judgment indicates that the first discomfort condition is satisfied and the result of the second judgment indicates that the second discomfort condition is satisfied, the process advances to step S15.

When the result of the first judgment indicates that the first discomfort condition is not satisfied or the result of the second judgment indicates that the second discomfort condition is not satisfied, the process ends.

Incidentally, when the judgment in the step S14 is No and the speaker 13 is outputting no masking sound, the sound masking control unit 180 does nothing. Namely, the sound masking control unit 180 executes control of outputting no masking sound. Thus, no masking sound is outputted from the speaker 13. When the judgment in the step S14 is No and the speaker 13 is already outputting masking sound, the sound masking control unit 180 executes control to continue the outputting of the masking sound.

(Step S15) The output judgment unit 170 judges that the masking sound should be outputted from the speaker 13. Specifically, when the speaker 13 is outputting no masking sound, the output judgment unit 170 judges that the masking sound should be outputted from the speaker 13 based on the acoustic features. When the speaker 13 is already outputting masking sound, the determination unit 181 determines to change the already outputted masking sound to new masking sound based on the acoustic features. Incidentally, the already outputted masking sound is referred to also as second masking sound. The new masking sound is referred to also as the first masking sound.

The determination unit 181 executes a determination process. For example, the determination unit 181 in the determination process determines the output direction of the masking sound, the volume level of the masking sound, the type of the masking sound, and so forth.

(Step S16) The output unit 182 has the masking sound outputted from the speaker 13 based on the determination process.

As above, the information processing device 100 is capable of putting the user U1 in a comfortable state by outputting the masking sound from the speaker 13.

As above, when it is judged that the masking sound should be outputted and masking sound is already being outputted from the speaker 13, the sound masking control unit 180 determines to change the already outputted masking sound to new masking sound and has the new masking sound outputted from the speaker 13. By this operation, the information processing device 100 is capable of putting the user U1 in the comfortable state.

Next, the process executed by the information processing device 100 will be described below by using a concrete example.

Figure 5:
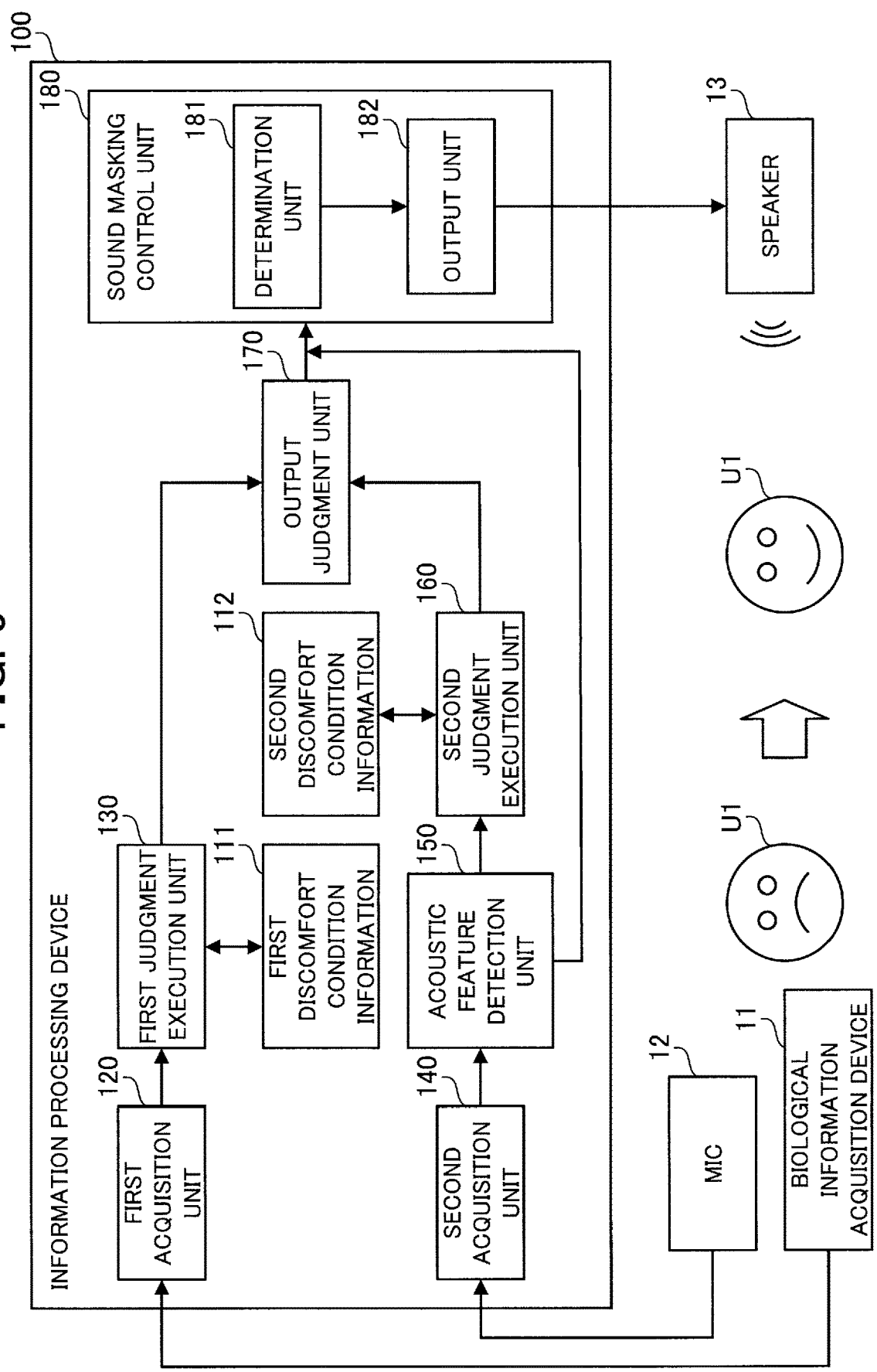
FIG. 5 is a diagram showing a concrete example of the process executed by the information processing device in the first embodiment.

FIG. 5 is a diagram showing a concrete example of the process executed by the information processing device in the first embodiment. FIG. 5 indicates that the information processing device 100 has first discomfort condition information 111 and second discomfort condition information 112. The first discomfort condition information 111 and the second discomfort condition information 112 have been stored in the storage unit 110.

The first discomfort condition information 111 indicates that discomfort exists when the active mass of the corrugator muscle is higher than or equal to the threshold value (i.e., when the glabella is wrinkled). The second discomfort condition information 112 indicates that discomfort exists when the frequency is 4 kHz or less, the sound pressure level is 6 dB or more higher than the background noise, and the fluctuation strength is high. As above, in FIG. 5, the second discomfort condition information 112 indicates the three elements as the second discomfort condition. Incidentally, the second discomfort condition can also be determined as one or more elements among the three elements. Further, in the second discomfort condition information 112, a condition that a frequency range is a wide range, a condition that the sound signal is occurring periodically, or a condition that the sound signal has temporal fluctuation may be added to the discomfort condition.

FIG. 5 indicates a situation in which a meeting has suddenly started in a front right direction from the user U1. This situation makes the user U1 uncomfortable.

The biological information acquisition device 11 acquires the active mass of the user U1's corrugator muscle. The first acquisition unit 120 acquires the active mass of the user U1's corrugator muscle from the biological information acquisition device 11. The active mass of the user U1's corrugator muscle is assumed to be greater than or equal to the threshold value indicated by the first discomfort condition information 111. The first judgment execution unit 130 judges that the first discomfort condition is satisfied. Namely, the first judgment execution unit 130 judges that the user U1 is feeling uncomfortable.

The mic 12 acquires sound. This sound includes voices from participants in the meeting or the like. The second acquisition unit 140 acquires the sound signal from the mic 12. The acoustic feature detection unit 150 detects the acoustic features based on the sound signal. The detected acoustic features indicate that the frequency is 4 kHz or less. The detected acoustic features indicate that the sound pressure level of the sound from the meeting is 48 dB. The detected acoustic features indicate that the fluctuation strength is high. Here, the acoustic feature detection unit 150 may also detect the sound pressure level of the background noise as an acoustic feature. For example, the acoustic feature detection unit 150 detects the sound pressure level of the background noise in a silent interval in the meeting. The sound pressure level of the background noise may also be measured previously. In FIG. 5, the sound pressure level of the background noise is assumed to be 40 dB. The second judgment execution unit 160 judges that the second discomfort condition is satisfied based on the detected acoustic features and the second discomfort condition information.

The output judgment unit 170 judges that the user U1 is feeling discomfort because of sound. The determination unit 181 acquires the acoustic features from the acoustic feature detection unit 150. The determination unit 181 determines the masking sound based on the acoustic features. For example, the determination unit 181 determines masking sound that is 4 kHz or lower. Further, the determination unit 181 determines the output direction of the masking sound based on the acoustic features. For example, the determination unit 181 determines that the masking sound should be outputted in the front right direction based on the direction in which the sound source exists. Furthermore, the determination unit 181 determines the sound pressure level based on the acoustic features. For example, the determination unit 181 may determine the sound pressure level at a sound pressure level lower than the sound pressure level of the sound from the meeting indicated by the acoustic feature. The determined sound pressure level is 42 dB, for example.

The output unit 182 has the masking sound outputted from the speaker 13 based on the result of the determination by the determination unit 181. The speaker 13 outputs the masking sound. By this process, the voices from the participants in the meeting or the like are masked. Then, the user U1 does not mind anymore the voices from the participants in the meeting or the like.

Further, also when the user U1 has become uncomfortable due to typing noise occurring in the vicinity of the user U1, for example, the information processing device 100 is capable of putting the user U1 in the comfortable state by executing a process like the above-described process.

According to the first embodiment, when the user U1 is feeling discomfort because of sound, the information processing device 100 has the masking sound outputted from the speaker 13. As above, the information processing device 100 is capable of executing sound masking control based on the user U1's condition.

The above description has been given of a case where the first judgment execution unit 130 judges whether the user U1 is uncomfortable or not by using one item of biological information. However, the first judgment execution unit 130 may also make the judgment on whether the user U1 is uncomfortable or not by using a plurality of items of biological information. For example, the plurality of items of biological information are the brain wave, the heart rate and the pulse wave. The process will be described in detail below. The first acquisition unit 120 acquires a plurality of items of biological information on the user U1. Here, the first discomfort condition information 111 specifies a plurality of discomfort conditions corresponding to the plurality of items of biological information. This sentence can also be expressed as follows: The first discomfort condition information 111 specifies a plurality of discomfort conditions using the plurality of items of biological information. As above, the plurality of discomfort conditions respectively correspond to the plurality of items of biological information. For example, the first discomfort condition information 111 indicates that discomfort exists when the brain wave is higher than or equal to a first threshold value, the heart rate is higher than or equal to a second threshold value, and the pulse wave is higher than or equal to a third threshold value. The first judgment execution unit 130 executes a third judgment on whether the plurality of discomfort conditions are satisfied or not based on the first discomfort condition information 111 and the plurality of items of biological information acquired by the first acquisition unit 120. The output judgment unit 170 judges that the masking sound should be outputted when the result of the second judgment indicates that the second discomfort condition is satisfied and the result of the third judgment indicates that the plurality of discomfort conditions are satisfied.

By using a plurality of items of biological information as above, the information processing device 100 is capable of precisely grasping the degree of discomfort the user U1 is feeling. Then, when the user U1 is feeling uncomfortable because of sound, the information processing device 100 has the masking sound outputted from the speaker 13. As above, the information processing device 100 is capable of executing sound masking control based on the user U1's condition.

Further, the first judgment execution unit 130 may also execute the first judgment on whether the first discomfort condition is satisfied or not based on a graph indicating the biological information and a graph indicating the first discomfort condition. The second judgment execution unit 160 may also execute the second judgment on whether the second discomfort condition is satisfied or not based on a graph indicating an acoustic feature and a graph indicating the second discomfort condition.

Second Embodiment

Next, a second embodiment will be described below. The following description of the second embodiment will be given mainly of differences from the first embodiment and items common to the first embodiment will be left out. FIGS. 1 to 4 will be referred to in the second embodiment.

Figure 6:
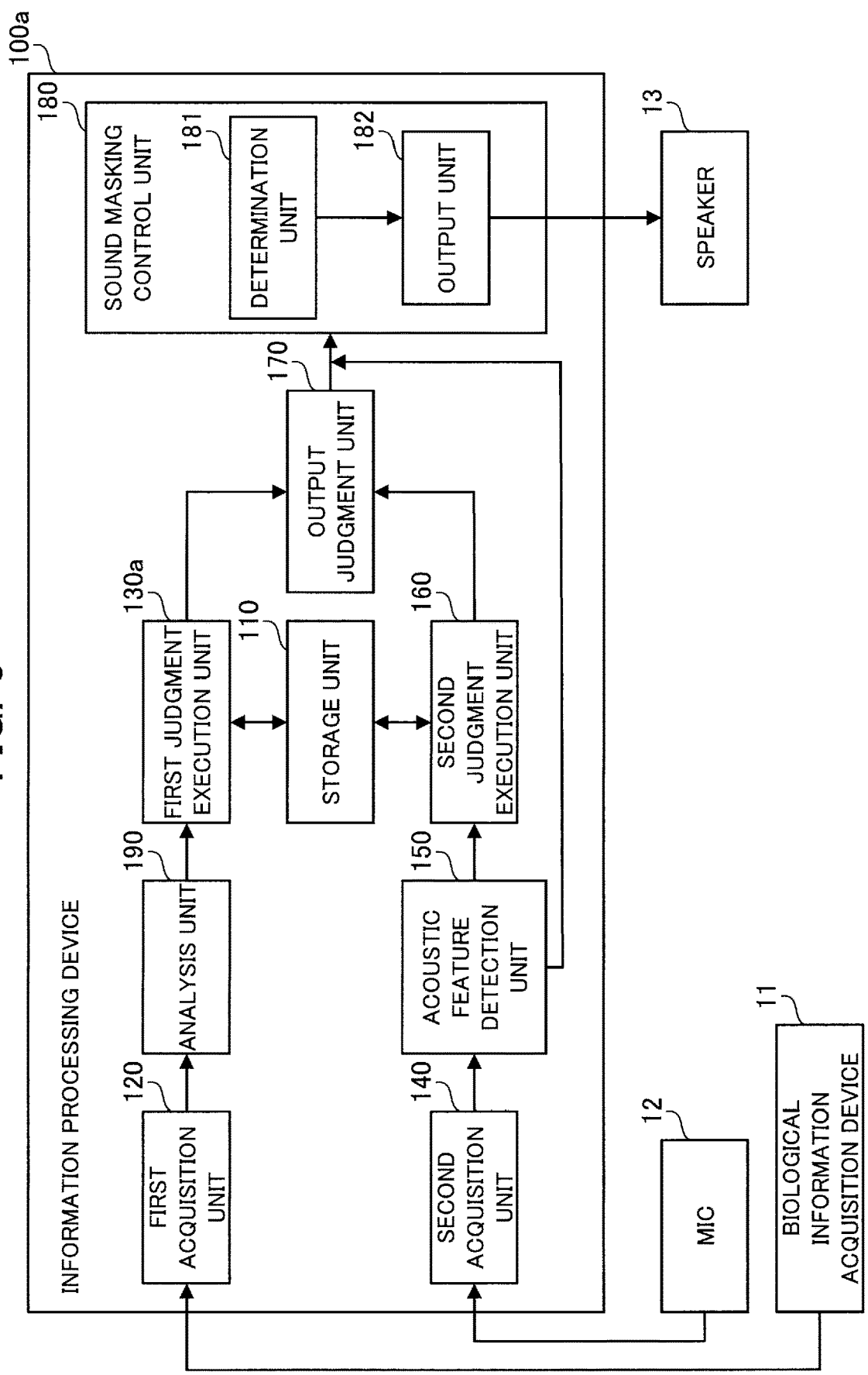
FIG. 6 is a functional block diagram showing a configuration of an information processing device in a second embodiment.

FIG. 6 is a functional block diagram showing the configuration of an information processing device in the second embodiment. The information processing device 100a includes an analysis unit 190 and a first judgment execution unit 130a.

Part or all of the analysis unit 190 and the first judgment execution unit 130a may be implemented by the processor 101. Part or all of the analysis unit 190 and the first judgment execution unit 130a may be implemented as modules of a program executed by the processor 101.

The analysis unit 190 analyzes the biological information. When the biological information is the heart rate, for example, the analysis unit 190 analyzes a Low Frequency (LF) and a High Frequency (HF) based on the information on the heart rate.

Here, the first discomfort condition specifies a discomfort condition based on a result of analysis of the biological information. For example, the first discomfort condition indicates that discomfort exists when LF/HF is higher than or equal to a threshold value.

The first judgment execution unit 130a executes the first judgment based on the result of the analysis by the analysis unit 190. For example, the first judgment execution unit 130a calculates LF/HF based on the LF and the HF analyzed by the analysis unit 190. When the calculated LF/HF is higher than or equal to the threshold value, the first judgment execution unit 130a judges that the user U1 is uncomfortable. Namely, the first judgment execution unit 130a judges that the first discomfort condition is satisfied.

The result of the first judgment by the first judgment execution unit 130a is acquired by the output judgment unit 170.

According to the second embodiment, when the user U1 is feeling discomfort because of sound, the information processing device 100a has the masking sound outputted from the speaker 13. As above, the information processing device 100a is capable of executing sound masking control based on the user U1's condition.

DESCRIPTION OF REFERENCE CHARACTERS

U1: user, 11: biological information acquisition device, 12: mic, 13: speaker, 100, 100a: information processing device, 101: processor, 102: volatile storage device, 103: nonvolatile storage device, 110: storage unit, 111: first discomfort condition information, 112: second discomfort condition information, 120: first acquisition unit, 130, 130a: first judgment execution unit, 140: second acquisition unit, 150: acoustic feature detection unit, 160: second judgment execution unit, 170: output judgment unit, 180: sound masking control unit, 181: determination unit, 182: output unit, 190: analysis unit.

What is claimed is:

1. An information processing device comprising:
a processor to execute a program; and
a memory to store the program which, when executed by the processor, performs processes of,
acquiring biological information on a user acquired by a biological information acquisition device;
executing a first judgment on whether a first discomfort condition as a discomfort condition corresponding to the biological information is satisfied or not based on first discomfort condition information specifying the first discomfort condition and the acquired biological information;
acquiring a sound signal outputted from a microphone;
detecting an acoustic feature based on the sound signal;
executing a second judgment on whether a second discomfort condition as a discomfort condition corresponding to the acoustic feature is satisfied or not based on second discomfort condition information specifying the second discomfort condition and the detected acoustic feature; and
judging whether first masking sound should be outputted or not based on a result of the first judgment and a result of the second judgment.

2. The information processing device according to claim 1, wherein the program which, when executed by the processor, performs a process of judging that the first masking sound should be outputted when the result of the first judgment indicates that the first discomfort condition is satisfied and the result of the second judgment indicates that the second discomfort condition is satisfied.

3. The information processing device according to claim 1, wherein a plurality of items of biological information on the user are acquired, the first discomfort condition information specifies a plurality of discomfort conditions corresponding to the plurality of items of biological information, the program which, when executed by the processor, performs processes of, executing a third judgment on whether the plurality of discomfort conditions are satisfied or not based on the first discomfort condition information and the plurality of items of biological information acquired, and judging that the first masking sound should be outputted when the result of the second judgment indicates that the second discomfort condition is satisfied and the result of the third judgment indicates that the plurality of discomfort conditions are satisfied.

4. The information processing device according to claim 1, wherein the program which, when executed by the processor, performs a process of analyzing the biological information, the first discomfort condition specifies a discomfort condition based on a result of analysis of the biological information, and the program which, when executed by the processor, performs a process of executing the first judgment based on a result of the analysis.

5. The information processing device according to claim 1, wherein the program which, when executed by the processor, performs a process of having the first masking sound based on the acoustic feature outputted from a speaker when it is judged that the first masking sound should be outputted.

6. The information processing device according to claim 5, wherein when it is judged that the first masking sound should be outputted and second masking sound is being outputted from the speaker, the program which, when executed by the processor, performs processes of determining to change the second masking sound to the first masking sound and having the first masking sound outputted from the speaker.

7. A sound masking system comprising:

a speaker; and an information processing device, wherein the information processing device includes:

a processor to execute a program; and a memory to store the program which, when executed by the processor, performs processes of, acquiring biological information on a user acquired by a biological information acquisition device;

executing a first judgment on whether a first discomfort condition as a discomfort condition corresponding to the biological information is satisfied or not based on first discomfort condition information specifying the first discomfort condition and the acquired biological information;

acquiring a sound signal outputted from a microphone;

detecting an acoustic feature based on the sound signal;

executing a second judgment on whether a second discomfort condition as a discomfort condition corresponding to the acoustic feature is satisfied or not based on second discomfort condition information specifying the second discomfort condition and the detected acoustic feature; and judging whether first masking sound should be outputted from the speaker or not based on a result of the first judgment and a result of the second judgment.

8. A control method performed by an information processing device, the control method comprising:

acquiring biological information on a user acquired by a biological information acquisition device, executing a first judgment on whether a first discomfort condition as a discomfort condition corresponding to the biological information is satisfied or not based on first discomfort condition information specifying the first discomfort condition and the acquired biological information, acquiring a sound signal outputted from a microphone, detecting an acoustic feature based on the sound signal, and executing a second judgment on whether a second discomfort condition as a discomfort condition corresponding to the acoustic feature is satisfied or not based on second discomfort condition information specifying the second discomfort condition and the detected acoustic feature; and judging whether first masking sound should be outputted or not based on a result of the first judgment and a result of the second judgment.

9. A non-transitory computer-readable recording medium storing a control program that causes an information processing device to execute a process of:

acquiring biological information on a user acquired by a biological information acquisition device, executing a first judgment on whether a first discomfort condition as a discomfort condition corresponding to the biological information is satisfied or not based on first discomfort condition information specifying the first discomfort condition and the acquired biological information, acquiring a sound signal outputted from a microphone, detecting an acoustic feature based on the sound signal, executing a second judgment on whether a second discomfort condition as a discomfort condition corresponding to the acoustic feature is satisfied or not based on second discomfort condition information specifying the second discomfort condition and the detected acoustic feature, and judging whether first masking sound should be outputted or not based on a result of the first judgment and a result of the second judgment.

* * * * *